United States Patent [19]

Simon

[11] 4,107,145
[45] Aug. 15, 1978

[54] SALTS OF BENZENEPHOSPHONIC ACID AND MELAMINE AS REACTIVE ADDITIVES TO FLAMMABLE EPOXY MONOMERS TO REDUCE FLAMMABILITY OF THE CURED REACTION PRODUCTS

[76] Inventor: Eli Simon, 7175 Little Harbor Dr., Huntington Beach, Calif. 92648

[21] Appl. No.: 820,810

[22] Filed: Aug. 23, 1977

Related U.S. Application Data

[62] Division of Ser. No. 663,446, Mar. 3, 1976, Pat. No. 4,061,605.

[51] Int. Cl.$^2$ ............................................. C08L 63/00
[52] U.S. Cl. .................................. 528/108; 528/118; 528/123; 528/405
[58] Field of Search ............ 260/47 EN, 2 N, 47 EC, 260/2 EC

[56] References Cited

U.S. PATENT DOCUMENTS

| | | | |
|---|---|---|---|
| 2,464,342 | 3/1949 | Pollak et al. | 427/379 |
| 3,050,522 | 8/1962 | Coates et al. | 260/249.6 |
| 3,134,742 | 5/1964 | Wismer et al. | 260/2.5 AJ |
| 3,296,265 | 1/1967 | Garner | 260/249.6 |
| 3,364,216 | 1/1968 | Johnson | 260/2.5 AJ |
| 3,400,085 | 9/1968 | Kujawa et al. | 260/2.5 AJ |
| 3,755,323 | 8/1973 | Weil et al. | 260/47 EN |
| 3,989,702 | 11/1976 | Garner | 260/249.6 |
| 4,003,861 | 1/1977 | Savides et al. | 260/45.8 NT |

Primary Examiner—M. J. Welsh

[57] ABSTRACT

This invention relates to the identification of salts of benzenephosphonic acid and melamine that are useful as additives for reducing the flame-propagation of normally flammable organo-polymers.

The physical and chemical properties of the benzenephosphonic acid-melamine addition products may be modified by varying the mol ratios of the reactants.

The salts of benzenephosphonic acid and melamine may be functionally inert or reactive when incorporated as additives, depending on their composition and the polymer system involved. Thus, applied to polyurethane foams, it is desirable that the additive be characterized as inert during the foaming reaction, whereas applied to monomeric-type epoxy systems, they may advantageously have the dual function of entering into the oxirane curing mechanism as well as imparting flame-retardency; in either case, the resultant products are unexpectedly and markedly improved in their resistance to flame initiation and flame propagation.

The flame-retardants of this invention have limited solubility in both polar and non-polar solvents, requiring that they be incorporated as dried, stabilized powders; if they can be tolerated in this form, they are applicable to any organo-polymeric system including those as coatings, adhesives, sealants, caulking compounds, and the like.

3 Claims, No Drawings

SALTS OF BENZENEPHOSPHONIC ACID AND MELAMINE AS REACTIVE ADDITIVES TO FLAMMABLE EPOXY MONOMERS TO REDUCE FLAMMABILITY OF THE CURED REACTION PRODUCTS

This is a division of Ser. No. 663,446, filed Mar. 3, 1976, and which is now U.S. Pat. No. 4,061,605.

BACKGROUND AND PRIOR ART

Many elements, such as nitrogen, phosphorous, arsenic, antimony, tin, bismuth, fluorine, chlorine, bromine, iodine, and boron can act as flame-retardants and, if when incorporated in selected chemical structures they become activated during an overheat condition, they can effectively interfere with the combustion reactions.

Flame-retardant additives vary widely in thermal stability, their effects on the flow behavior of the organo-polymer, and in the corrosivity and toxicity of the products of thermal and hydrolytic decompositions. Thermal stability not only affects the eventual capacity of the additive as a fire-retardant but also the more immediate consequences of corrosivity of the decomposition is premature. The liberation of corrosive gases is characteristic of the halogenated additives, flow behavior by the type of additive, i.e., non-plasticizing vs plasticizing, and toxicity to the action of specific chemical by-products on living tissue; in particular, toxicity is complicated by relationships to the conditions of pyrolysis such as temperature, length of heating time, oxidizing or reducing, as well as material composition.

The elimination of halogenated compounds was considered desirable as they are major contributors to corrosivity as well as toxicity; their by-products are represented by phosgene, halogen acids, and related compounds. The elimination of antimony oxide, particularly in conjunction with a halogen, was considered desirable to reduce both the toxicity and corrosivity of the antimony trichloride and/or the oxychloride formed at temperatures above approximately 600° F. Phosphate esters contribute to reduced thermal stability, high flow indices and the concomitant possibility of fire spread, with secondary effects of toxicity and corrosivity of the vapor phase products.

In assessing the characteristics of fire-retardant additives, the degree of development of smoke, or smoke obscuration, must be considered as this can reduce vision and lead to panic in a fire situation. In this regard, smoke is considered to be an airborne mixture of heated gases, liquid droplets, and solid particles; in addition to reducing vision, it may act as an irritant causing tissue injury by heat and chemical reaction. Thus, by illustration, although adequate retardency of flame propagation can be achieved using mixtures of antimony oxide, a brominated epoxy and a halogenated plasticizer, the resultant smoking can be so heavy as to preclude its acceptability for use in aircraft interiors.

A melamine pyrophosphate, used as an aqueous suspension, is reported in U.S. Pat. No. 2,464,342 (1949) for imparting flame resistance to textile fibers. The degree of improvement obtained by the subject disclosure when benzenephosphonic acid was substituted as the acidic hydrogen donor for the melamine amine group was unexpected, and appears consistent for various mol ratios of benzenephosphonic acid to melamine.

It is an object of this invention to provide additives that will reduce the defects of corrosivity and toxicity inherent in the currently used fire-retardants.

SUMMARY OF THE INVENTION

This invention discloses reaction products of benzenephosphonic acid and melamine that are effective as additives for reducing the flame initiation and flame propagation of flammable organo-polymers, functioning either as non-reactive constituents or as reactive components of the formulations; as the designation implies, for the non-reactive applications, the additive remains essentially as a separate constituent in contrast to the reactive application in which it becomes an integral part of the polymer chain.

DESCRIPTION OF THE INVENTION

The fire-retardants of this invention comprise aqueous reaction products between benzenephosphonic acid and melamine within the mol-percent range of 33⅓% to 66⅔% of benzenephosphonic acid and preferably within the range of 33⅓% to 40 mol-percent of benzenephosphonic acid.

The fire retardants are conceptualized, but not limited to the mechanism proposed, as addition products formed between the amino group(s) of melamine and the acidic hydroxyl group(s) of benzenephosphonic acid, as noted in the following:

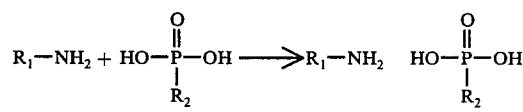

where, $R_1$ is the connecting ring structure of melamine (or the diamino-s-trizine) residue, and $R_2$ is the phenyl group.

The procedure used in the preparation of the addition products included the steps of predissolving the benzenephosphonic acid in hot (up to boiling) distilled water, adding the melamine powder slowly with continuous agitation to the hot solution, maintaining heating and stirring for approximately 15–30 minutes, cooling, filtering and drying the precipitate to constant weight at approximately 120° C. Moisture removal may be accomplished at ambient or reduced pressures or by spray drying. Recrystallization is readily accomplished, if desired, by dissolving the compound in a sufficient volume of hot (preferably boiling) distilled distilled water, cooling, filtering, removing the bulk water from the crystals, and drying to constant weight at approximately 120° C.

The ratio of two moles of benzenephosphonic acid to three moles of melamine, and one mole of benzenephosphonic acid to two moles of melamine, appears unique in its pronounced thickening capacity when dispersed in water, either as-formed during the addition of melamine to the aqueous solution of benzenephosphonic acid or as a post-effect with each of the recovered reaction products.

Differences in crystal structure of the salts, particularly within the range of 33⅓ to 40 mol-percent of benzenephosphonic acid, and their components are readily apparent, the addition-products being slender and needle-like in contrast to the more prismatic forms of the melamine and benzenephosphonic acid.

As the mol percent of the benzenephosphonic acid in the salt increases, the pH of its saturated distilled water solution decreases and the solubility in distilled water increases; thus, for the mol percent range of 66⅔% to 33⅓%, these varied respectively from approximately pH 2.0 to 4.7, and the solubility at 70° F. (g/100 ml. of sol'n.) from approximately 2.4 to 0.5. These physical properties are sufficiently diverse to provide a wide range of applicability depending in part on whether the fire-retardant is to function as an inert additive or as a reactive component. In addition, the limited aqueous solubility adds to the stability of the treated polymer system both with regard to post-leaching and hydrolytic effects.

The addition product salts are incorporated as finely divided, dried powders: when applied to a polyurethane foaming system, they may be added at the time of mixing of the reactive components, or pre-mixed with the non-isocyanate component as part of a masterbatch; when applied to a castable polymer system, they may be introduced, as would a pigment, using suitable grinding equipment such as a ball mill, roller mill, etc; when used as a reactive component, such as with monomeric polyoxiranes, they may be mixed with the epoxy at the time of use for 100% solid compositions, or dispersed in a solvent solution of the epoxy (for a one-package composition), or in the catalyst component (for a two-package composition).

EXAMPLES OF THE INVENTION

EXAMPLE 1

Benzenephosphonic Acid-Melamine Addition Product Salts As Flame-Retardants For Polyurethane Foamed Plastics (a) Polyurethane Foam — CPR's (division of the Upjohn Company) Isocyanate 2018, a two component flexible polyurethane foam having a free rise density of approximately 3 pounds per cubic foot.

(b) Benzephosphonic acid-melamine salt additives — mol ratios of 2:3, 1:1, 1:2, and 3:2 respectively.

(c) Weight percent of the "salt" additives — five to twenty-five wt.% of the total, or approximately 5.3 to 33.3 parts of additive per 100 parts of foam mix.

Flame retardency was evidenced for all of the cases noted, using a Fisher-type of burner as the igniting source, with best results for the mol ratios of benzenephosphonic acid to melamine of 2:3 and 1:2 respectively at a preferred weight percentage loading of at least 10%. These results are in marked contrast to the behavior of the cured foam without additive, which when tested in the same manner showed rapid flaming and vigorous flame propagation.

For the mol ratio of benzenephosphonic acid to melamine greater than 50%, the acidity of the salt, used as a flame-retardant additive in polyurethane foaming systems, would have to be compensated by the addition of alkaline neutralizing agents, such as a tertiary amine.

The applicability of the benzenephosphonic acid-melamine addition products as flame-retardants was further demonstrated by the relative ineffectiveness of a 25 wt.% loading of equal parts by weight of borax, sodium metaphosphate, sodium metasilicate, and aluminum sulfate (either to inhibit flame initiation or flame propagation) when incorporated in the flexible polyurethane foam system previously noted.

EXAMPLE 2

Stability To Moisture Leaching Of Benzenephosphonic Acid-Melamine Salt

A benzenephosphonic acid-melamine having a mol ratio of 2:3 respectively was used as an additive to CPR's foaming system of Example 1. at a 25 wt.% of the total weight. A sample of the cured foam, with all faces freshly cut, weighing 2.25 grams was totally immersed in 60 ml. of distilled water for 26.5 hours at ambient temperature. After drying to constant weight at 250° F., the foam showed no impairment in resisting flame initiation or flame propagation when soaked in the flame of a Fisher-type burner.

EXAMPLE 3

Test Of Benzenephosphonic Acid And Melamine As Neat Additives To A Polyurethane Foaming System Benzenephosphonic acid and melamine were added without prior reaction to the polyurethane foam of Example 1. in a mol ratio of 2:3 respectively and a combined weight percentage of 25 of the total weight of the components. This resulted in almost complete collapse of the foam, inadequately cured, in contrast to results in Examples 1 and 2 in which there was no adverse effect on the foaming reaction for the same weight percentage and mol ratio of the additive when prereacted.

EXAMPLE 4

Test Of A Melamine Phosphate Salt As An Additive To A Polyurethane Foaming System The melamine phosphate was prepared by reacting melamine and 85% phosphoric acid in a mol ratio of 1:1. The recovered product incorporated as an additive at a 25 wt.% of the total in the foaming system of Example 1., had no apparent adverse effect on the foaming results but its effectiveness as a flame-retardant was considerably inferior to the benzenephosphonic acid-melamine salts of this invention.

EXAMPLE 5

Benzenephosphonic Acid-Melamine Addition Product Salt As Flame-Retardant For Rigid Polyurethane Foamed Plastics This is an extension of Example 1. in which a rigid polyurethane foam is substituted for the flexible foam. At a 25 wt.% (of the total), the salt of 2 moles benzenephosphonic acid to 3 moles melamine changed the cured foam (CPR's Isocyanate 380) from one easily ignited with vigorous flame propagation, to one that was self-quenching.

EXAMPLE 6

Benzenephosphonic Acid-Melamine Addition Product Salts As Flame-Retardant Reactants In An Epoxy System A benzenephosphonic acid-melamine salt in the mol ratio of 1:2 respectively was used as a curing agent for a diepoxide at ⅛, 3/16, ¼, ½, ¾, and 1-mole of the "salt" to 1-mole of Shell Epon 826, a liquid diglycidyl ether of bisphenol A having an epoxy equivalent of 180–188; in addition, for the ratio of ½ mol benzenephosphonic acid-melamine salt to one mol Epon 826, 10.25 g. DMP-30, tris(dimethylaminomethyl-phenol), was added per oxirane equivalent.

Curing tests showed that the amine-catalyzed composition could be cured at less than 125° C., and that those without DMP-30 required a cure temperature of approximately 150° C.

Flammability tests of the cured specimens showed that a preferred ratio of reactant "salt" to epoxy of greater than ⅛ to one mol of Epon 826, or a weight percentage of greater than approximately 12, imparted effective flame-retardation to the cured system; 10 weight percent of the reactive additive, based on the total weight of the components, appears to be a practical approximate minimum for acceeptable reduction of support of combustion. Those compositions that did not support combustion contained from approximately 20 to 50 weight percent of "salt" of the total weight of the components. The best from the combined properties of flame-retardation and physical characteristics was the composition of ¼ mol "salt" to one mol Epon 826, or approximately 22 wt.% "salt", based on the total weight of the components.

I claim:

1. Cured reaction products having reduced flammability prepared by reacting polyfunctional epoxy monomers with benzenephosphonic acid-melamine salts, said salts being prepared by reacting benzenephosphonic acid with melamine in a mol ratio of benzenephosphonic acid to melamine of from 1-mol of benzenephosphonic acid : 2-mols of melamine to 2-mols of benzenephosphonic acid : 3-mols of melamine.

2. Cured reaction products of claim 1 containing at least 10 weight percent of the benzenephosphonic acid-melamine salts, based on the total weight of the components.

3. Cured reaction products of claim 1 containing from 12–50 weight percent of the benzenephosphonic acid-melamine salts, based on the total weight of the components.

* * * * *